(12) United States Patent
Lin et al.

(10) Patent No.: US 11,844,842 B2
(45) Date of Patent: Dec. 19, 2023

(54) COMPOSITION OF POLYETHYLENE GLYCOL MALEIMIDE DERIVATIVE AND POLYMERIZATION INHIBITOR

(71) Applicant: JenKem Technology Co., Ltd. (Beijing), Beijing (CN)

(72) Inventors: Meina Lin, Beijing (CN); Xuan Zhao, Beijing (CN)

(73) Assignee: JenKem Technology Co., Ltd. (Beijing), Beijing (CN)

( * ) Notice: Subject to any disclaimer, the term of this patent is extended or adjusted under 35 U.S.C. 154(b) by 121 days.

(21) Appl. No.: 17/558,819

(22) Filed: Dec. 22, 2021

(65) Prior Publication Data

US 2022/0143200 A1    May 12, 2022

Related U.S. Application Data

(63) Continuation-in-part of application No. 16/588,246, filed on Sep. 30, 2019, now Pat. No. 11,220,559, which is a continuation of application No. PCT/CN2018/077231, filed on Feb. 26, 2018.

(30) Foreign Application Priority Data

Mar. 31, 2017  (CN) .......................... 201710209106.6
Jun. 30, 2017  (CN) .......................... 201710530958.5

(51) Int. Cl.

| | | |
|---|---|---|
| C08F 2/40 | (2006.01) | |
| C08K 5/24 | (2006.01) | |
| C08K 5/13 | (2006.01) | |
| C08K 5/098 | (2006.01) | |
| C08K 3/16 | (2006.01) | |
| C08F 16/28 | (2006.01) | |
| A61K 47/34 | (2017.01) | |
| A61K 47/60 | (2017.01) | |
| C08G 65/333 | (2006.01) | |
| A61K 47/02 | (2006.01) | |
| A61K 47/10 | (2017.01) | |
| A61K 47/08 | (2006.01) | |
| A61K 47/54 | (2017.01) | |

(52) U.S. Cl.
CPC .............. *A61K 47/60* (2017.08); *A61K 47/02* (2013.01); *A61K 47/08* (2013.01); *A61K 47/10* (2013.01); *A61K 47/545* (2017.08); *C08G 65/33396* (2013.01)

(58) Field of Classification Search
CPC ... C08F 2/40; C08F 16/28; C08K 5/24; C08K 3/16; C08K 5/13; C08K 5/098; A61K 47/34; A61K 47/60; A61K 47/54; A61K 47/10; A61K 47/08; A61K 47/02; C08G 65/333
See application file for complete search history.

(56) References Cited

U.S. PATENT DOCUMENTS

| | | | |
|---|---|---|---|
| 5,045,233 A † | 9/1991 | Kita | |
| 2011/0142787 A1 | 6/2011 | Nagasaki | |
| 2011/0286956 A1 † | 11/2011 | Zhao | |
| 2012/0282671 A1 * | 11/2012 | Zhao | ................. C08G 65/3322 435/188 |

FOREIGN PATENT DOCUMENTS

| | | | |
|---|---|---|---|
| CN | 1858085 A | | 11/2006 |
| CN | 101724144 A | † | 6/2010 |
| CN | 103275670 A | | 9/2013 |
| CN | 103373949 A | | 10/2013 |
| CN | 104877127 A | | 9/2015 |
| CN | 105348530 A | | 2/2016 |

OTHER PUBLICATIONS

Charles M. Rubert Pérez et al.; Turning the thermosensitive properties of hybrid collagen peptide-polymer hydrogels; Chemical communications; Jun. 5, 2014; p. 8174-8176; England.
Leo L. Wang et al.; Injectable, Guest-Host Assembled Polyethylenimine Hydrogel for siRNA Delivery; Biomacromolecules; Dec. 5, 2016; p. 77-86; US.
8-Arm PEG—Creative PEGWorks; PEGWorks; Jan. 12, 2017; p. 4; Online.
First Office Action for Chinese Serial No. 201710530958.5; dated Apr. 19, 2019.
Second Office Action for Chinese Serial No. 201710530958.5; dated Oct. 29, 2019.
Supplementary European Search Report for European serial No. 18774544.3; dated Mar. 4, 2020.
International Search Report for PCT app No. PCT/CN2018/077231; dated May 30, 2018.
Written Opinion of the International Searching Authority for app No. PCT/CN2018/077231; dated May 30, 2018.
Catalog of Creative PEGWorks, Apr. 11, 2015, pp. 1-43 (Creative PEGWorks Catalog).†
Creative PEGWorks, 8-Arm PEG—Creative PEGWorks, Jan. 12, 2017, 1 page, XP055679993, retrieved from internet: URL:https://web.archive.org/web/20170112091416/http://www.creativepegworks.com/product_list.php?cid=8&pid=2&sid=14 [retrieved on Mar. 26, 2020] (Creative PEGWorks 1).†
Creative PEGWorks, 8-Arm PEG-MAL, Mar. 26, 2020, 1 page, XP055680002, Retrieved from the Internet: URL:http://www.creativepegworks.com/product_view.php?cid=8&pid=2&sid=14&id=861 [retrieved on Mar. 26, 2020] (Creative PEGWorks 2).†

(Continued)

*Primary Examiner* — Robert D Harlan

(74) *Attorney, Agent, or Firm* — FLENER IP & BUSINESS LAW; Zareefa B. Flener

(57) ABSTRACT

The present invention provides a composition of a polyethylene glycol maleimide derivative and a polymerization inhibitor. In particular, the present invention provides a composition of an 8-arm polyethylene glycol maleimide derivative and a phenolic polymerization inhibitor. The ingredient and content of the polymerization inhibitor in the composition are reasonably chosen, thereby significantly increasing stability of the polyethylene glycol maleimide derivative, effectively avoiding the undesirable effect of gel solidifying due to polymerization during storage and transportation, and extending a pot life and shelf life of a product thereof.

17 Claims, 3 Drawing Sheets

(56) References Cited

OTHER PUBLICATIONS

Homepage (Q&A site) of Creative PEGWorks (Effective date: Sep. 3, 2014), 1 page, retrieved from internet: URL:https://web.archive.org/web/20140903063114/http://creativepegworks.com/faq.php (Creative PEGWorks Q&A).†
Perez et al., Tuning the thermosensitive properties of hybrid collagen peptide-polymer hydrogels, Chemical Communications (Cambridge, England), Jun. 5, 2014, 50, pp. 8174-8176, XP055679971, and Supporting Information.†
Wang et al, Injectable, Guest-Host Assembled Polyethylenimine Hydrogel for siRNA Delivery, Biomacromolecules, vol. 18, No. 1, Dec. 5, 2016, pp. 77-86, XP055680009.†

\* cited by examiner
† cited by third party

COMPOSITION OF POLYETHYLENE GLYCOL MALEIMIDE DERIVATIVE AND POLYMERIZATION INHIBITOR

CROSS-REFERENCE TO RELATED APPLICATIONS

This application is a continuation-in-part of U.S. application Ser. No. 16/588,246, filed on Sep. 30, 2019, which is a continuation of International Application No. PCT/CN2018/077231, filed on Feb. 26, 2018. The International Application claims priority to Chinese patent application No. CN201710209106.6 filed on Mar. 31, 2017 and CN201710530958.5 field on Jun. 30, 2017 respectively. All of the aforementioned applications are hereby incorporated by reference in their entireties.

TECHNICAL FIELD

The invention relates to the technical field of polymers, in particular to a composition of a polyethylene glycol maleimide derivative and a polymerization inhibitor, in more particular to an eight-arm polyethylene glycol maleimide derivative and a phenol. A composition of a class of polymerization inhibitors.

BACKGROUND TECHNIQUE

Polyethylene glycol (PEG) is a non-toxic, amphiphilic macromolecular compound formed by polymerization of ethylene glycol monomers. PEG modification is a technology developed from the late 1970s. To solve many problems in the clinical application of some drugs such as peptides and protein drugs, some PEG modified products have achieved good results when used in a drug. The hydroxyl group at the end of the polyethylene glycol is a functional group for its chemical reaction, but the reactivity is poor, and a derivative of polyethylene glycol which is activated in an appropriate way is often used as a modifier. The activated terminal groups such as amino, carboxyl, aldehyde, maleimide and the like play a decisive role in the application of polyethylene glycol. Different terminal groups have different uses, and the introduction of these reactive groups expands the application range of PEG. For polyethylene glycol maleimide derivative (PEG-MAL), a maleimide group is introduced into PEG, and the coupling of maleimide and sulfhydryl group is one of useful reactions to couple protein and polypeptide. PEG-MAL can be used as a polymer reagent to selectively trap thiol-containing peptides. Sulfhydryl group(s) can be introduced into specific sites of a peptide and a protein by genetically engineering, and PEG-MAL can be further used for site-specific modification. The selectivity of the modification is high, and the loss of biological activity of the protein could be avoided, and in the meanwhile the immunogenicity could be lowered. In recent years, it has been found that PEG-MAL plays a key role in the linkage between proteins or peptides and liposomes. PEG-MAL is of great significance for targeting liposomes and for expanding the application of peptide compounds in medicine and biotechnology. Therefore, PEG-MAL is a polyethylene glycol derivative with a very high application value.

However, the maleimide derivative of polyethylene glycol contains an unsaturated double bond which has a high reaction activity, resulting in poor stability of the derivative, and polymerization at room temperature often occurs at room temperature to form a gel-like insoluble matter. This would cause the content of the derivative to be low, and the shelf life is short, leading to great inconvenience to its preservation and transportation, thereby limiting its application.

SUMMARY OF THE INVENTION

The inventors of the present application have found through extensive experiments and studies that a polyethylene glycol maleimide derivative (especially an eight-arm polyethylene glycol maleimide derivative) and some polymerization inhibitors can be combined to enhance its stability or reduce its photosensitivity, extending product pot life and shelf life.

In one aspect, the invention provides a composition of a polyethylene glycol maleimide derivative and a polymerization inhibitor.

In the composition, the mass ratio of the polymerization inhibitor to the polyethylene glycol maleimide derivative is ≥0.1 µg:1 g.

In one embodiment of the present invention, the mass ratio of the polymerization inhibitor to the polyethylene glycol maleimide derivative may be from 0.1 µg to 10 mg:1 g, such as 0.1 to 100 µg.:1 g (eg, 0.1 µg:1 g, 1 µg:1 g, 5 µg:1 g, 10 µg:1 g, 20 µg:1 g, 30 µg:1 g, 40 µg:1 g, 50 µg:1 g, 60 µg, 70 µg:1 g, 80 µg:1 g, 90 µg:1 g or 100 µg:1 g), 100 µg-1 mg:1 g (eg, 100 µg:1 g, 200 µg:1 g, 300 µg:1 g, 400 µg:1 g, 500 µg:1 g, 600 µg:1 g, 700 µg:1 g, 800 µg:1 g, 900 µg:1 g or 1 mg:1 g), 1-10 mg:1 g (eg, 1 mg:1 g, 2 mg:1 g, 3 mg:1 g, 4 mg:1 g, 5 mg:1 g, 6 mg:1 g, 7 mg:1 g, 8 mg:1 g, 9 mg:1 g or 10 mg:1 g); preferably 1 µg to 1 mg:1 g.

In the composition, the polyethylene glycol maleimide derivative contains at least one terminal maleimide group.

In one embodiment of the invention, the polyethylene glycol maleimide derivative has the following structure:

PEG-X-MAL                                    (I)

Wherein PEG is a polyethylene glycol residue,
X is a linking group of PEG and MAL, and is selected from: one or a combination of two or more of —(CH$_2$)$_r$—,

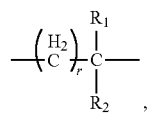

—(CH$_2$)$_r$O—, —(CH$_2$)$_r$CO—, —(CH$_2$)$_r$NH—, —(CH$_2$)$_r$CONH—, —(CH$_2$)$_r$NHCO—, —(CH$_2$)$_r$S—, —(CH$_2$)$_r$COO— and —(CH$_2$)$_r$OCO—, r is an integer from 0 to 10, MAL is a maleimide group

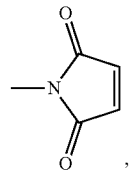

,

R$_1$ and R$_2$ are independently selected from the group consisting of: —H, a C1-6 alkyl group, a C1-6 alkoxy group, a C3-6 cycloalkyl group, and a C4-10 alkylene cycloalkyl group.

Preferably, said R$_1$ and R$_2$ are independently selected from the group consisting of: —H, —CH$_3$, —CH$_2$CH$_3$, —CH$_2$CH$_3$, —CH$_2$CH$_2$CH$_3$, —OCH$_3$, —OCH$_2$CH$_3$ and —OCH₂CH₂CH₃, more preferably from: —H, —CH₃, —OCH₃ and —OCH₂CH₃; In a preferred embodiment of the invention, R₁ is H, R₂ is —CH₃, —OCH₃ or —OCH₂CH₃; in a more preferred embodiment of the invention, R₁ is H and R₂ is —CH₃.

In a specific embodiment of the invention, the X is selected from the group consisting of: one or a combination of two or more of a single bond, —CH₂—, —CH₂CH₂—, —CH₂CH₂CH₂—, —CH₂CH₂CH₂CH₂—, —CH₂CH₂CH₂CH₂CH₂—, —CH(CH₃)—, —CH₂CH(CH₃)—, —CH₂CH₂CH(CH₃)—, —CH₂CH₂CH₂CH(CH₃)—, —CH₂CH₂CH₂CH₂CH(CH₃)—, —CH₂CH₂CH₂CH₂CH₂CH(CH₃)—, —(CH₂)ᵣO—, —(CH₂)ᵣCO—, —(CH₂)ᵣNH—, —(CH₂)ᵣCONH—, —(CH₂)ᵣNHCO—, —(CH₂)ᵣS—, —(CH₂)ᵣCOO— and —(CH₂)ᵣOCO—.

In a preferred embodiment of the invention, the X is selected from the group consisting of: one or a combination of two or more of a single bond, —CH₂—, —CH₂CH₂—, —CH₂CH₂CH₂—, —CH(CH₃)—, —CH₂CH(CH₃)—, —CH₂CH₂CH(CH₃)—, —(CH₂)ᵣCO—, —(CH₂)ᵣNH—, —(CH₂)ᵣCONH— and —(CH₂)ᵣNHCO—.

In one embodiment of the invention, r is an integer from 0 to 5, such as 0, 1, 2, 3, 4 or 5.

In a more preferred embodiment of the invention, the X is —CH₂CH₂NHCOCH₂CH₂—.

In the composition of the present invention, the PEG may be a linear, Y- or multi-branched polyethylene glycol residue, for example, including a linear polyethylene glycol, a Y- or U-shape PEG, and a 4-arm branched PEG, 6-arm branched PEG or 8-arm branched PEG, and the like.

In one embodiment of the invention, the PEG is a linear polyethylene glycol residue having the structure shown in Formula II or III:

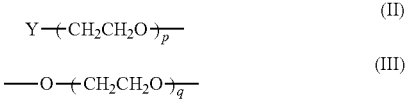

wherein Y is a terminal group selected from the group consisting of: C1-C6 alkoxy group, hydroxyl, carboxyl group, succinimide carbonate group, succinimide acetate group, succinimide propionate group, and a succinyl group. Imine succinate group, succinimide group, dithiopyridyl group, propionic acid group, aldehyde group, thiol ester group, acryloxy, acrylic acid group, azido group, glutaric acid group, alkynyl, p-nitrogen one of a phenyl carbonate group, silane, and carboxymethyl; p and q are independently selected from an integer of from 1 to 1400, preferably from 1 to 1200, more preferably from 200 to 1200.

In one embodiment of the invention, in Formula II, said Y is methoxy.

In one embodiment of the invention, the PEG is a Y- or U-shape polyethylene glycol residue having the structure shown in Formula IV or V:

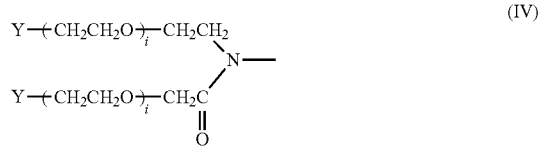

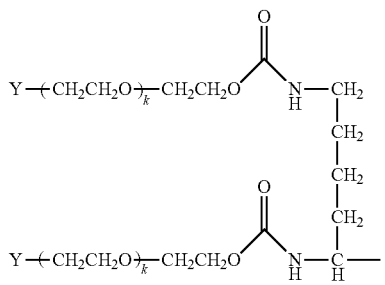

Wherein Y is a terminal group having the above definition of the present invention, i and k are independently selected from an integer from 1 to 1200, preferably from an integer from 1 to 600, more preferably from 100 to 600.

In one embodiment of the invention, in Formula IV and/or V, said Y is methoxy.

In one embodiment of the invention, the PEG is a multi-branched polyethylene glycol residue having the structure shown in Formula VI:

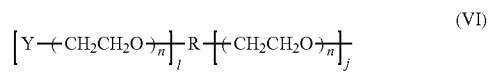

Wherein Y is an terminal group having the above definition of the present invention, n is an integer from 1 to 800, preferably an integer from 1 to 400, more preferably an integer from 60 to 400, l is an integer from 0 to 7, and j is an integer from 1 to 8; preferably, $3 \leq j+1 \leq 8$, R is a core molecule of a multi-branched polyethylene glycol, and R is selected from the group consisting of: pentaerythritol, oligopentaerythritol, methyl glucoside, sucrose, diethylene glycol, propylene glycol, glycerin, and polyglycerol residues.

In one embodiment of the invention, in Formula VI, said Y is methoxy.

In one embodiment of the invention, the l is zero.

In a preferred embodiment of the invention, the PEG is a multi-branched polyethylene glycol residue, and the polyethylene glycol maleimide derivative has the following structure:

In one embodiment of the invention, the polyethylene glycol maleimide derivative has the following structure:

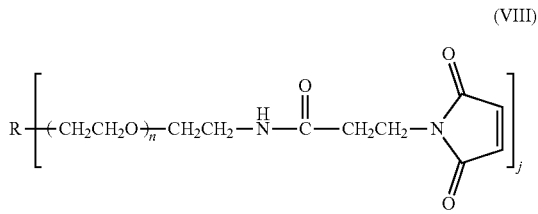

Preferably, in formula VIII, j=8, the PEG is an eight-arm polyethylene glycol residue, and the polyethylene glycol maleimide derivative is an eight-arm polyethylene glycol maleimide derivative.

In a specific embodiment of the present invention, in formula VIII, j=8, the R has the structure represented by formula IX or X:

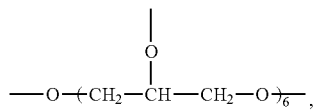

(IX)

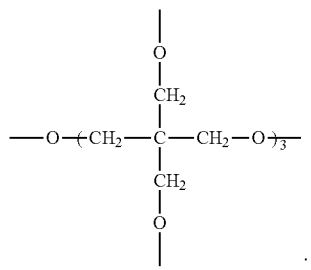

(X)

In a preferred embodiment of the invention, the polyethylene glycol maleimide derivative has the following structure:

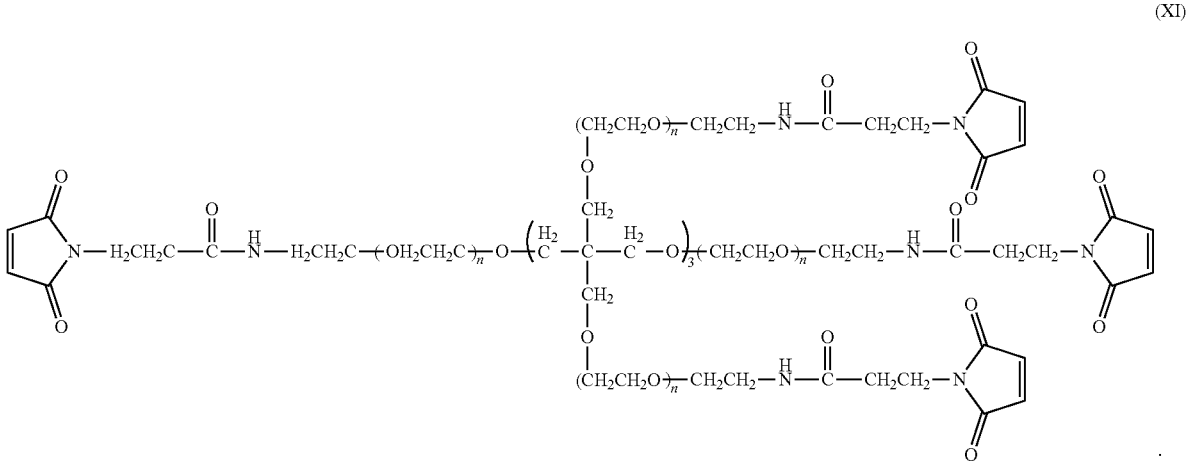

(XI)

In one embodiment of the present invention, the PEG may have a molecular weight of 1-80 KDa, such as 1-10 KDa (specifically 1, 2, 3, 4, 5, 6, 7, 8, 9, or 10 KDa), 10-80 KDa (specifically 10, 15, 20, 25, 30, 35, 40, 45, 50, 60, 70 or 80 KDa); preferably 10-50 KDa.

In a preferred embodiment of the invention, the PEG has a molecular weight of 10 KDa, 20 KDa or 40 KDa.

In the present invention, the polymerization inhibitor is a substance which converts a primary radical or a chain radical into a stable molecule or to form a stable radical which is low in activity and which is insufficient for the polymerization to proceed. It will be understood by those skilled in the art that the polymerization inhibitor can be classified into the following categories based on the substituent(s): free radicals, phenols, quinones, aromatic amines, nitro compounds, a nitroso compound, sulfur-containing compounds, inorganic compounds, or organometallic compounds, oxygens, etc. (see Xiao Weidong, He Benqiao, He Peixin. Chemical additives for polymer materials. Beijing: Chemical Industry Press, 2003: 331-341").

In one embodiment of the present invention, the polymerization inhibitor is selected from one or a combination of two or more of a radical polymerization inhibitor, a phenolic polymerization inhibitor, an inorganic compound polymerization inhibitor, and an organometallic compound polymerization inhibitor.

In one embodiment of the present invention, the radical polymerization inhibitor includes, but not limited to, one or more of 1,1-diphenyl-2-picrylyl radical (1,1-Diphenyl-2-picrylhydrazyl, DPPH), nitroxide radicals such as 4,4'-dimethoxydiphenylnitroxyl radical (4,4'-dimethoxydiphenyl oxynitride, DMDPN), 4,4'-dinitrodiphenylnitroxyl radical (4,4'-dinitrodiphenyl oxynitride), di-tert-butyl nitroxyl radical (di-tert-butyl oxynitride, DTBNO), 2,2,6,6-tetramethyl-4-hydroxypiperidine nitroxyl radical (2,2,6,6-tetramethyl-4-hydroxypiperidine oxynitride, TEMPO), benzoyl peroxide (BPO).

In a specific embodiment of the invention, the radical polymerization inhibitor is DPPH.

In one embodiment of the present invention, the phenolic polymerization inhibitor includes, but not limited to, one or more of hydroquinone, p-tert-butyl phenol, methyl hydroquinone, p-tert-butyl catechol, p-hydroxybenzene. Methyl ether, 2-tert-butyl hydroquinone, 2,5-di-tert-butyl hydroquinone, 2,6-di-tert-butyl-4-methylphenol (BHT), 4,4'-dihydroxybiphenyl, pyrogallol and bisphenol A.

In a preferred embodiment of the invention, the phenolic polymerization inhibitor is hydroquinone and/or p-tert-butyl phenol.

In one embodiment of the present invention, the inorganic compound polymerization inhibitor includes, but is not limited to, one or more of ferric chloride, cuprous chloride, copper chloride, copper sulfate, titanium trichloride, titanium chloride, sodium sulfate, sodium sulfide and ammonium thiocyanate.

In a specific embodiment of the invention, the inorganic compound inhibitor is copper chloride.

In one embodiment of the invention, the organometallic compound polymerization inhibitor includes, but not limited to, one or more of copper naphthenate, chromium acetate, nickel acetate, copper dimethyl dithiocarbamate, and copper dit-butyl dithiocarbamate.

In a specific embodiment of the invention, the organometallic compound polymerization inhibitor is nickel acetate.

The inventors of the present invention have experimentally found that the combination of phenolic polymerization inhibitors (such as hydroquinone and p-t-butyl phenol) and polyethylene glycol maleimide derivatives (especially eight-arm polyethylene glycol maleimide derivatives) can significantly enhance the stability, reduce the photosensitivity, and extend the shelf life and storage period of the derivatives, and the effect is better than other combinations of polyethylene glycol maleimide derivatives with other polymerization inhibitors.

In a preferred embodiment of the present invention, in the composition, the polymerization inhibitor is a phenolic polymerization inhibitor. Preferably the polymerization inhibitor is selected from: one or a combination of two or more of hydroquinone, p-t-butyl phenol, methyl hydroquinone, tert-butyl catechol, 2-tert-butyl hydroquinone, 2,5-di-tert-butyl hydroquinone, 4-methoxyphenol, 2,6-di-tert-butyl-4-methylphenol, 4,4'-dihydroxybiphenyl, pyrogallol and bisphenol A. More preferably, the polymerization inhibitor is hydroquinone or p-tert-butyl-phenol.

In a preferred embodiment of the invention, in the composition, the polyethylene glycol maleimide derivative has the structure of the above formula VIII, wherein, preferably, j=8, more preferably, the R has the structure of the above formula IX or X, and most preferably, the polyethylene glycol maleimide derivative has the structure of the above formula XI; preferably, the molecular weight of the PEG is 1-80 KDa, for example, 1-10 KDa (specifically 1, 2, 3, 4, 5, 6, 7, 8, 9 or 10 KDa), 10-80 KDa (specifically 10, 15, 20, 25, 30, 35, 40, 45, 50 60, 70 or 80 KDa), more preferably 10-50 KDa, most preferably 10 KDa, 20 KDa and 40 KDa; in the composition, the polymerization inhibitor is a phenolic polymerization inhibitor, and preferably is selected from: one or more of hydroquinone, p-tert-butyl-phenol, methyl hydroquinone, p-tert-butyl catechol, 2-tert-butyl hydroquinone, 2,5-di-tert-butyl hydroquinone, 4-methoxyphenol, 2,6-di-tert-butyl-4-methylphenol, 4,4'-dihydroxybiphenyl, pyrogallol and bisphenol A, more preferably the polymerization inhibitor is hydroquinone or tert-butyl Phenol; in the composition, the mass ratio of the phenolic polymerization inhibitor and the polyethylene glycol maleimide derivative may be from 0.1 µg to 10 mg:1 g, such as from 0.1 to 100 µg (eg, 0.1 µg, 1 µg, 5 µg:1 g, 10 µg:1 g, 20 µg:1 g, 30 µg:1 g, 40 µg:1 g, 50 µg:1 g, 60 µg:1 g, 70 µg:1 g, 80 µg:1 g, 90 µg:1 g, 100 µg:1 g), 100 µg-1 mg:1 g (eg, 100 µg:1 g, 200 µg:1 g, 300 µg:1 g, 400 µg:1 g, 500 µg:1 g, 600 µg:1 g, 700 µg:1 g, 800 µg:1 g, 900 µg:1 g, 1 mg:1 g), 1-10 mg:1 g (eg, 1 mg:1 g, 2 mg:1 g, 3 mg:1 g, 4 mg:1 g, 5 mg:1 g, 6 mg:1 g, 7 mg:1 g, 8 mg:1 g, 9 mg:1 g, 10 mg:1 g).

In a more preferred embodiment of the invention, in the composition, the polymerization inhibitor is a phenolic polymerization inhibitor, preferably is hydroquinone or p-tert-butyl-phenol, the polyethylene glycol maleimide derivative has the structure of the above formula VIII of the present invention, and the mass ratio of the phenolic polymerization inhibitor to the polyethylene glycol maleimide derivative may be from 1 µg to 1 mg:1 g.

Another aspect of the invention also provides the use of a composition as described above for the preparation of a pharmaceutical conjugate.

Another aspect of the present invention also provides a pharmaceutical composition comprising a polymerization inhibitor and a conjugate of a polyethylene glycol maleimide derivative of the present invention and a drug.

Preferably, the polymerization inhibitor is a phenolic polymerization inhibitor, more preferably is selected from: one or more of hydroquinone, p-t-butyl phenol, methyl hydroquinone, p-tert-butyl catechol, 2-tert-butyl hydroquinone, 2,5-di-tert-butyl hydroquinone, 4-methoxyphenol, 2,6-di-tert-butyl-4-methylphenol, 4,4'-dihydroxybiphenyl, pyrogallol and bisphenol A, most preferably the polymerization inhibitor is hydroquinone and/or p-tert-butyl-phenol.

In one embodiment of the invention, the drug is selected from one or more of amino acids, polypeptides, proteins, sugars, organic acids, alkaloids, flavonoids, terpenoids, terpenoids, phenylpropanoid phenols, steroids, and quinones.

In a specific embodiment of the invention, the drug is a polypeptide or protein drug.

In a specific embodiment of the invention, the polypeptide or protein drug contains a free sulfhydryl group.

In another embodiment of the invention, a sulfhydryl group is introduced at a specific site in the polypeptide or protein drug.

In a specific embodiment of the present invention, the polypeptide or protein drug includes, but is not limited to, a polypeptide hormone, a polypeptide cell growth regulator, other biochemical drugs containing a polypeptide component, a protein hormone, a plasma protein, and a protein cell growth regulators, mucins, lectins, antibodies and enzymes such as a urea oxidase.

In one embodiment of the invention, the polypeptide hormones include, but are not limited to, pituitary polypeptide hormones (such as corticotropin, melatonin, lipolysis hormone, oxytocin, etc.), hypothalamic hormones (such as thyrotropin releasing hormone), auxin inhibitory hormone, gonadotropin-releasing hormone, etc.), thyroid hormone (such as parathyroid hormone, calcitonin, pancreas hormone: glucagon, pancreatic spasmolytic polypeptide, etc.), gastrointestinal hormones (such as gastrin, cholecystokinin-trypsin, vasoactive intestinal peptide, etc.) and thymus hormones (such as thymosin, thymus serum factor, etc.).

In one embodiment of the invention, the polypeptide cell growth regulators include, but are not limited to, epidermal growth factor, transfer factor, and atrial natriuretic peptide.

In one embodiment of the present invention, the other biochemical drugs containing a polypeptide component include, but are not limited to, Ossotide, Ocustrilla Extracti Oculi, soleosery, Antaisu, Fuxuening, brain aminopeptide, bee venom, snake venom, embryonic hormone, cofactor, neurotrophic factor, placental extract, pollen extract, spleen hydrolysate, liver hydrolysate and cardiac hormone.

In one embodiment of the present invention, the protein hormone includes, but is not limited to, pituitary protein hormones (such as auxin, prolactin, thyrotropin, luteinizing hormone, follicle stimulating hormone, etc.), gonadotropin (such as human chorionic gonadotropin, serotonin, etc.) and insulin and other protein hormones such as relaxin.

In one embodiment of the invention, the plasma protein includes, but is not limited to, albumin, plasminogen, plasma fibronectin, immunoglobulin, fibrinogen, and coagulation factors.

In one embodiment of the invention, the proteinaceous cell growth regulators include, but are not limited to, interleukin (IL-1 to IL-38), colony stimulating factor (eg, granulocyte colony stimulating factor (G-CSF)), macrophage colony-stimulating factor (M-CSF), granulocyte and macrophage colony-stimulating factor (GM-CSF), multi-colony stimulator (Multi-CSF), stem cell factor (SCF), erythropoietin (EPO)), interferon ($\alpha$, $\beta$, $\gamma$), growth factors (such as epidermal growth factor, platelet-derived growth factor, fibroblast growth factor, hepatocyte growth factor, insulin-like growth factor, nerve growth factor, platelet-derived) Endothelial growth factor, vascular endothelial growth factor, transforming growth factor-α, etc., tumor necrosis factor, tissue plasminogen activator and erythropoietin.

In one embodiment of the invention, the mucin comprises, but is not limited to, gastric factor, collagen, a basic protein, and a protease inhibitor such as a trypsin inhibitor.

In one embodiment of the invention, the lectin includes, but is not limited to, concanavalin, wheat germ, peanut agglutinin, soybean lectin, and the like.

In one embodiment of the invention, the antibodies include, but are not limited to, anti-CD20 antibodies, antibodies against the EGFR family (eg, anti-EGFR antibodies, anti-HER-2 antibodies), and anti-VEGF/VEGFR antibodies, and the like.

In one embodiment of the invention, the enzyme includes, but is not limited to, L-asparaginase, glutaminase, urokinase, neuraminidase, superoxide dismutase, and the like.

Another aspect of the invention also provides a pharmaceutical conjugate prepared as described above.

Another aspect of the invention also provides the use of the polymerization inhibitor in the preparation of the above compositions, pharmaceutical combinations and pharmaceutical compositions.

Preferably, in the above application, the polymerization inhibitor is a phenolic polymerization inhibitor, more preferably, the polymerization inhibitor is selected from: one or more of hydroquinone, p-t-butyl phenol, methyl hydroquinone, p-tert-butyl catechol, 2-tert-butyl hydroquinone, 2,5-di-tert-butyl hydroquinone, 4-methoxyphenol, 2,6-di-tert-butyl-4-methylphenol, 4,4'-dihydroxybiphenyl, pyrogallol and bisphenol A. Most preferably, the polymerization inhibitor is hydroquinone and/or p-tert-butyl phenol.

The invention provides a composition of a polyethylene glycol maleimide derivative and a polymerization inhibitor, in particular a combination of an eight-arm polyethylene glycol maleimide derivative and a phenolic polymerization inhibitor (such as hydroquinone and p-tert-butyl-phenol), wherein the structure and content of the polymerization inhibitor could be selected reasonably, and the stability of the polyethylene glycol maleimide derivative can be greatly enhanced, thereby effectively avoided adverse effect of gelation during the periods of transportation and storage, prolong the pot life and storage period of the product, and is effective for preparing drug conjugates, especially polypeptide (polypeptidic) and protein (proteinaceous) drug conjugates.

DRAWINGS

FIGS. 5A and 5B show the GPC detection spectrum in Example 5, wherein FIG. 5A is the GPC detection spectrum with hydroquinone, and FIG. 5B is the GPC detection spectrum without hydroquinone.

DETAILED DESCRIPTION OF THE INVENTION

Figure 1:
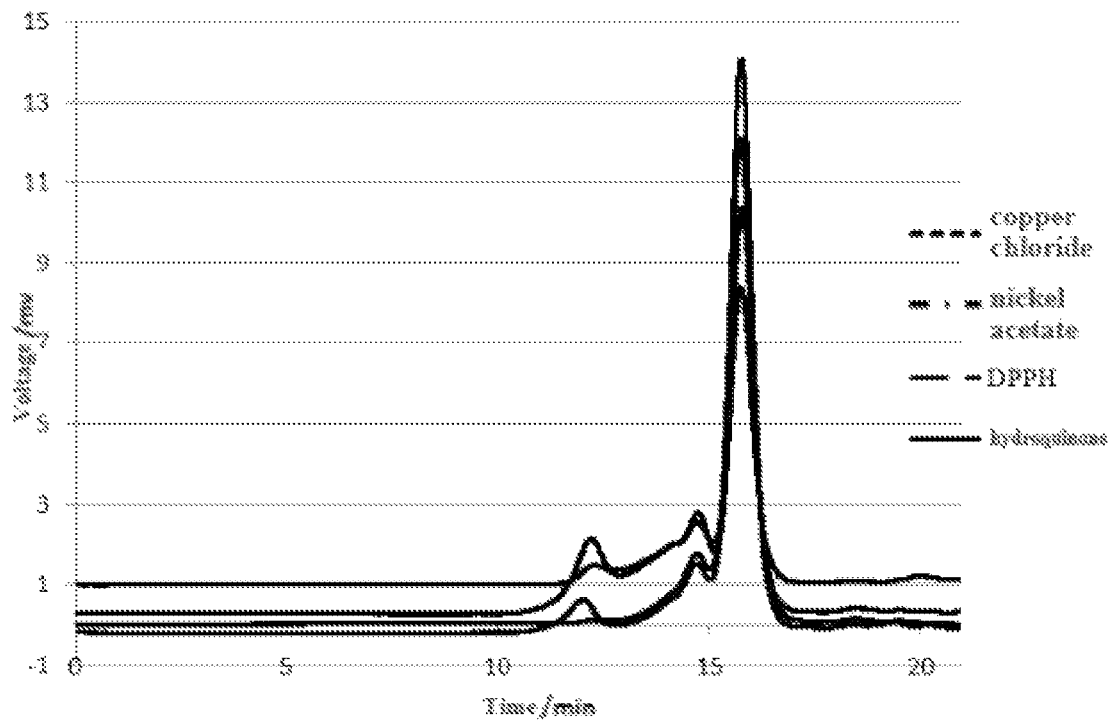
FIG. 1 shows the GPC pattern of 8ARM(TP)-PEG-MAL-40K with a polymerization inhibitor added after 2 days irradiation.

Unless defined otherwise, all technical and scientific terms used in the present invention have the same meaning as commonly understood by one of ordinary skill in the art to which this invention pertains.

"Alkyl" refers to a hydrocarbon chain radical that is linear or branched and free of unsaturated bonds. The $C_1$-$C_6$ alkyl means an alkyl having 1 to 6 carbon atoms, such as methyl, ethyl, n-propyl, isopropyl, n-butyl, isobutyl, t-butyl, n-pentyl, isopentyl, neopentyl, tert-amyl, n-hexyl, isohexyl and the like.

"Alkoxy" means a substituent formed by substituting the hydrogen in hydroxy group with an alkyl group, and C1-C6 alkoxy group means an alkoxy group having 1 to 6 carbon atoms, such as methoxy or ethoxy, propoxy, butoxy, and the like.

"Cycloalkyl" means an alicyclic hydrocarbon, such as those containing 1 to 4 monocyclic and/or fused rings. It may contain 3 to 18 carbon atoms, preferably 3 to 10 carbon atoms, such as cyclopropyl, cyclohexyl or adamantyl and the like. C3-C6 cycloalkyl in the present invention means a cycloalkyl having 3 to 6 carbon atoms, such as cyclopropyl, cyclobutyl, cyclopentyl and cyclohexyl.

In addition, some specific groups and their chemical structures involved in the present invention correspond to the following: hydroxyl group, —OH;

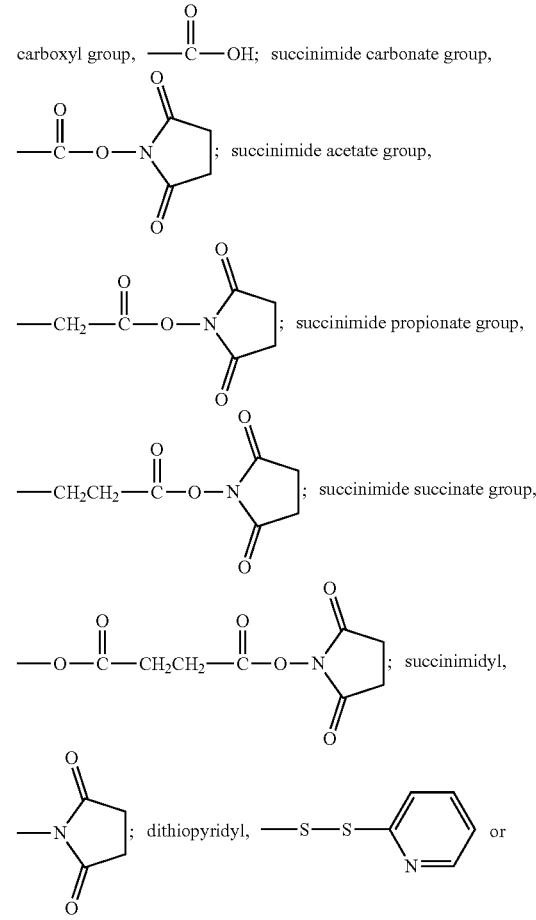

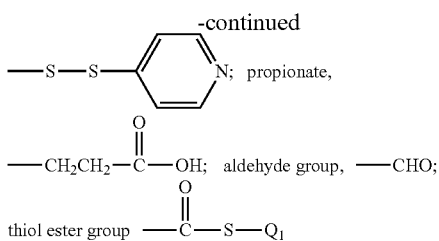; propionate,

—CH₂CH₂—C(=O)—OH; aldehyde group, —CHO;

thiol ester group —C(=O)—S—Q₁

(wherein Q₁ may be an alkyl group or a heterocyclic group such as methyl, ethyl, n-propyl, tert-butyl, pyridyl (such as

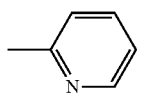

etc.);

acrylate, —CH=CH—C(=O)—OH;

acrylate (acryloyloxy), —O—C(=O)—CH=CH₂;

azide, —N⁺=N=N⁻ (-N₃);

glutarate, such as

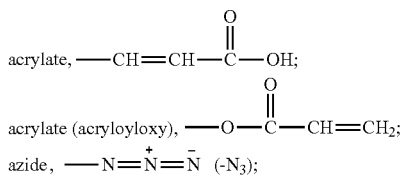 alkynyl

—C≡CH; p-nitrophenyl carbonate,

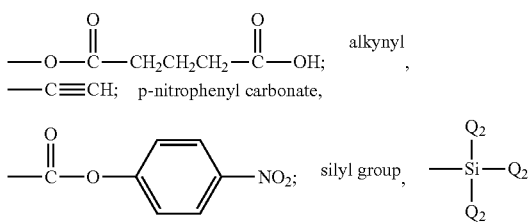; silyl group, —Si(Q₂)(Q₂)—Q₂

(wherein Q₂ may be the same or different alkyl or alkoxy group, such as methyl, ethyl, propyl, butyl, pentyl, methoxy, ethoxy, propyl Oxyl, butoxy, etc., preferably, Q₂ is methyl, ethyl, n-propyl, methoxy, ethoxy, n-propoxy, etc.);

carboxymethyl, 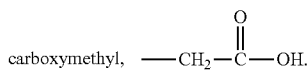.

In the definition of a linking group in the present invention, the "combination" means a group formed by linking two or more of the listed linking groups by a chemical bond. For example, the combination of —(CH₂)ᵣ— and —(CH₂)ᵣNHCO— may be —(CH₂)ᵣNHCO(CH₂)ᵣ— and specifically, the combination of —CH₂— and —CH₂CH₂NHCO— may be —CH₂CH₂NHCOCH₂—, —CH₂CH₂CH₂NHCO—. The "combination" is used to define the chemical structure of the linking group, and does not involve the preparation steps, the order of linking groups in the combination, etc.

The polyethylene glycol maleimide derivative described in the present invention is a polyethylene glycol to which a maleimide group is attached, as shown in formula I of the present invention, specifically as shown in formula XI; the linkage can be achieved by a covalent bond or by a linking group, and the reaction for achieving the linkage is well known to those skilled in the art, which is not specifically defined in the present invention.

The "composition of a polyethylene glycol maleimide derivative and a polymerization inhibitor" described in the present invention may further contain other components, such as ultraviolet absorbers (UV-P) to improve product quality or function. Those skilled in the art can add other components according to actual needs. Moisture, impurities and the like are inevitably involved in the process of production, transportation or storage of the polyethylene glycol maleimide derivatives and the compositions thereof and these substances are not specifically defined in the present invention.

The technical solutions of the present invention will be described clearly and completely with reference to the embodiments of the present invention. It is obvious that these embodiments are only a part of the possible embodiments of the present invention, and not all of the embodiments.

All other embodiments obtained by a person of ordinary skill in the art based on the embodiments of the present invention without involvement of inventive step are within the scope of the present invention.

The compounds used in the present invention are either commercially available or can be prepared according to the disclosed preparation methods, which are not meant to limit the scope of the invention.

The polyethylene glycol derivative used in the examples was supplied by JENKEM Technology Co., Ltd. (Beijing). All others are commercially available reagents.

Example 1

Hydroquinone, DPPH, nickel acetate, copper chloride and was respectively obtained and mixed with 8ARM(TP)-PEG-MAL-40K (250 mg) to form composition powders, wherein hydroquinone, DPPH, nickel acetate and copper chloride were all at 100 ppm.

The above composition powders were separately placed in a watch glass and placed in a light box at a constant temperature (2750 Lux, 18.5° C.) for two days, and the GPC results are shown in FIG. 1.

According to FIG. 1, the GPC concentration or content comparison results after 2 days of irradiation of 8ARM(TP)-PEG-MAL-40K (to which a polymerization inhibitor was added) are shown in Table 1.

TABLE 1

GPC concentration or content after 2 days irradiation of 8ARM(TP)-PEG-MAL-40K with polymerization inhibitor added

| | Addition of a polymerization inhibitor | | | |
|---|---|---|---|---|
| | hydroquinone | DPPH | nickel acetate | copper chloride |
| 8ARM(TP)-PEG-MAL-40K purity(%) | 83.9 | 77.3 | 67.9 | 54.3 |

As shown in Table 1, among the above four polymerization inhibitors, with the addition of hydroquinone, 8ARM (TP)-PEG-MAL-40K had the lowest degree of purity reduction, with the best inhibiting effect.

Example 2

Different types and concentrations or content of additives were obtained and mixed with 8ARM(TP)-PEG-MAL-40K (250 mg) to form composition powders: hydroquinone, p-tert-butyl-phenol, a mixture of hydroquinone and UV absorber (hydroquinone & UV-P, the mass ratio is 1:1), DPPH, nickel acetate, copper chloride, wherein the concentrations or content of each additive were at 1, 20, 100, 400 and 1000 ppm.

Figure 2:
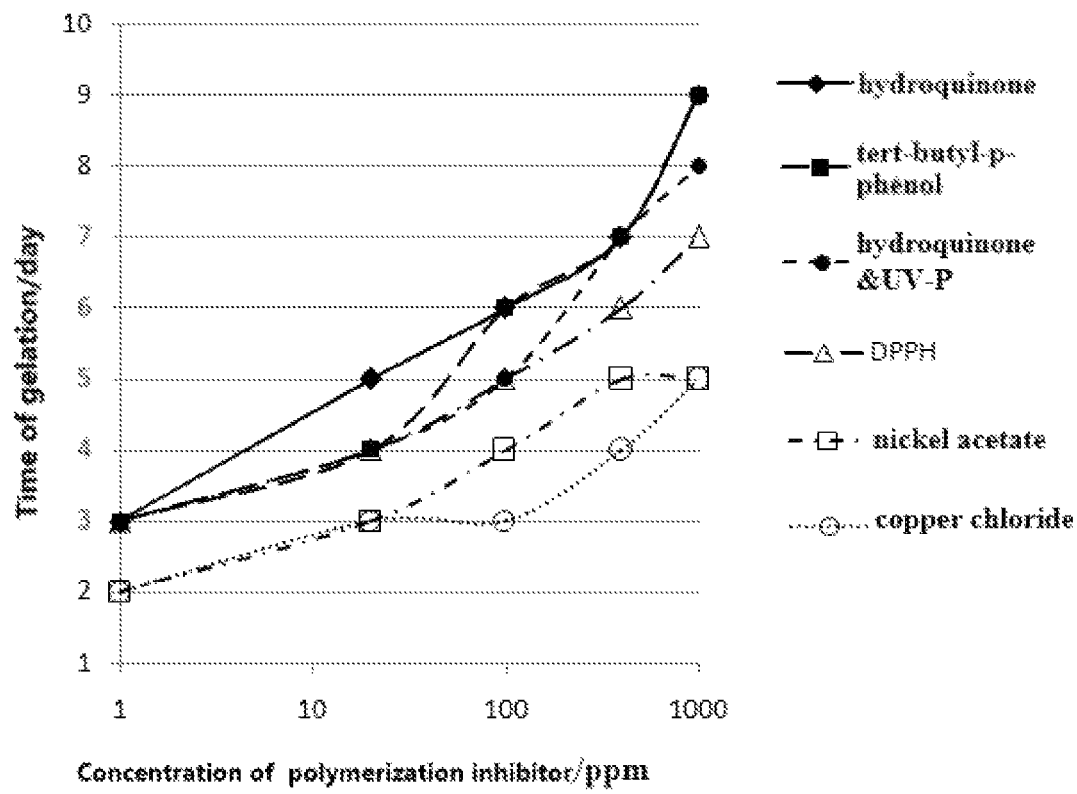
FIG. 2 shows the effect of the type and concentration or content of the polymerization inhibitor on the time of 8ARM(TP)-PEG-MAL-40K before the complete deterioration.

The above composition powders were separately placed in a watch glass and placed in a light box at a constant temperature (2750 Lux, 18.5° C.) to record the time required before complete deterioration (i.e., when a gel insoluble in methanol occurred), and the result was as shown in FIG. 2 (Note: If no additives were added, 8ARM(TP)-PEG-MAL-40K were completely deteriorated after two days of irradiation).

It can be seen from FIG. 2 that the effect of phenolic polymerization inhibitors such as hydroquinone and p-tert-butyl-phenol are better than the other polymerization inhibitors, and the mixture of hydroquinone and UV-P has the similar effect as that of hydroquinone alone.

Example 3

Composition powders containing different concentrations or content of hydroquinone, DPPH, nickel acetate, copper chloride and 8ARM(TP)-PEG-MAL-20K (250 mg), were separately taken, wherein the concentration or content of each polymerization inhibitor were at 1, 20, 100, 400, 1000 ppm.

Figure 3:
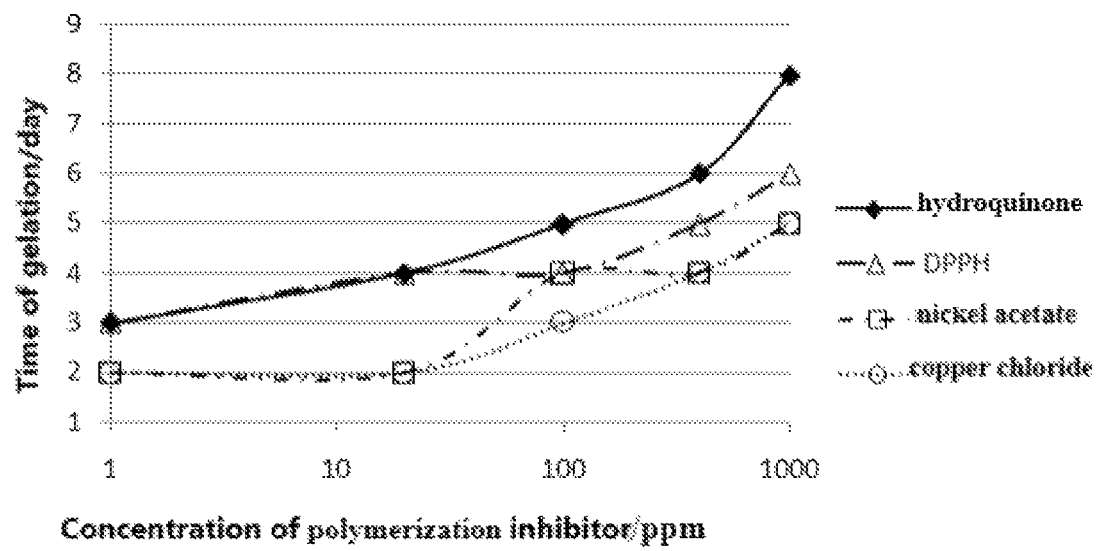
FIG. 3 shows the effect of the type and concentration or content of the polymerization inhibitor on the time of 8ARM(TP)-PEG-MAL-20K before the complete deterioration.

The above composition powders were separately placed in a watch glass and placed in a light box at a constant temperature (2750 Lux, 18.5° C.) to record the time required before complete deterioration (i.e., when a gel insoluble in methanol occurred), and the result was as shown in FIG. 3 (Note: If no inhibitor is added, 8ARM(TP)-PEG-MAL-20K would completely deteriorate after two days of irradiation).

Example 4

A composition powder containing different concentrations or content of hydroquinone, DPPH, nickel acetate, copper chloride and 8ARM(TP)-PEG-MAL-10K (250 mg) was separately taken, wherein the concentration or content of each polymerization inhibitor was at 1, 20, 100, 400, 1000 ppm.

Figure 4:
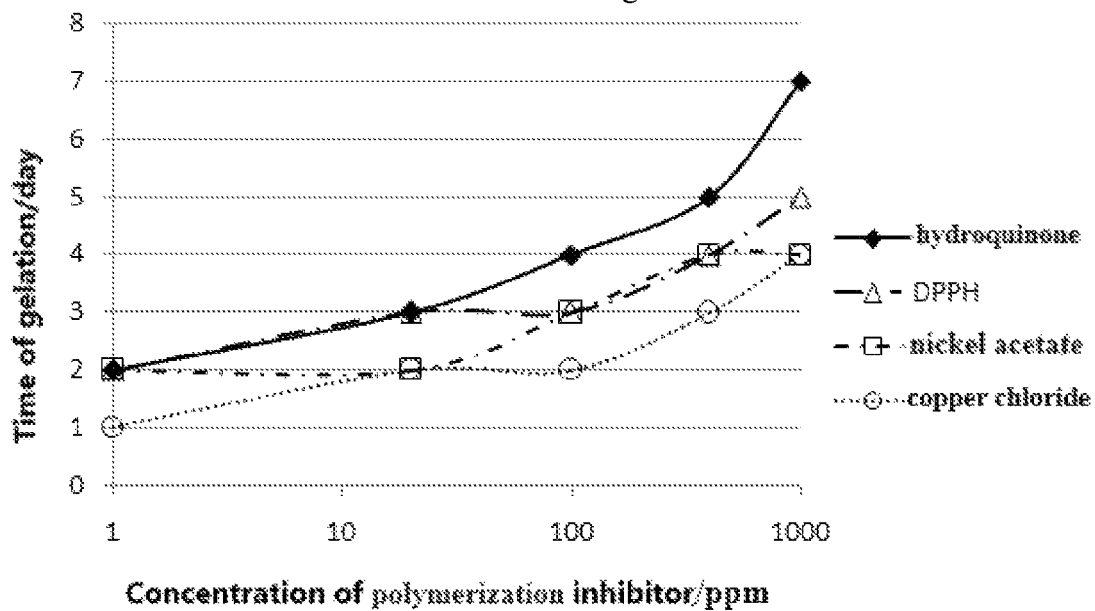
FIG. 4 shows the effect of the type and concentration or content of the polymerization inhibitor on the time of 8ARM(TP)-PEG-MAL-10K before the complete deterioration.

The above composition powders were separately placed in a watch glass and placed in a light box at a constant temperature (2750 Lux, 18.5° C.) to record the time required before complete deterioration (i.e., a gel insoluble in methanol occurred), and the result was as Shown in FIG. 4 (Note: If no inhibitor is added, 8ARM(TP)-PEG-MAL-10K would completely deteriorate after one day of irradiation).

It can be seen from Examples 2-4 that the above polymerization inhibitors, particularly hydroquinone, have a good stabilizing effect on polyethylene glycol maleimide derivatives of different molecular weights.

The 8ARM(TP)-PEG-MAL used in the embodiment of the present invention has the following structure:

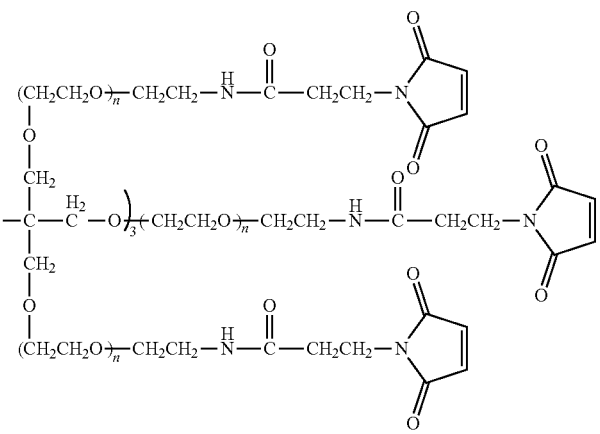

Enhanced stability, prolonged pot life and storage period could be achieved all the same for the maleimide derivative of polyethylene glycol of other configurations and molecular weights, when mixed with the polymerization inhibitor in the examples of the present invention. Those experimental data are not shown herein.

Example 5

Figure 5A:
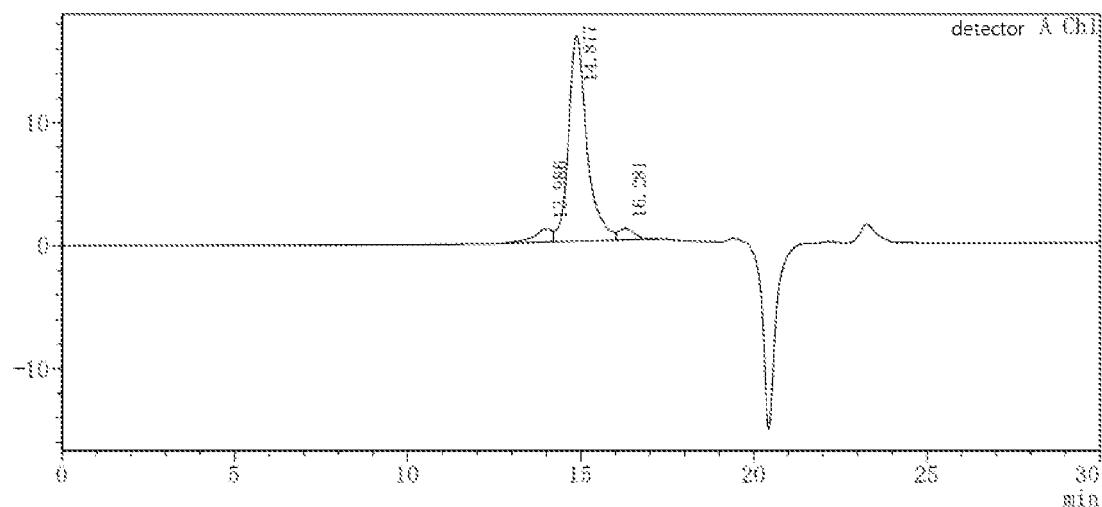
Figure 5B:
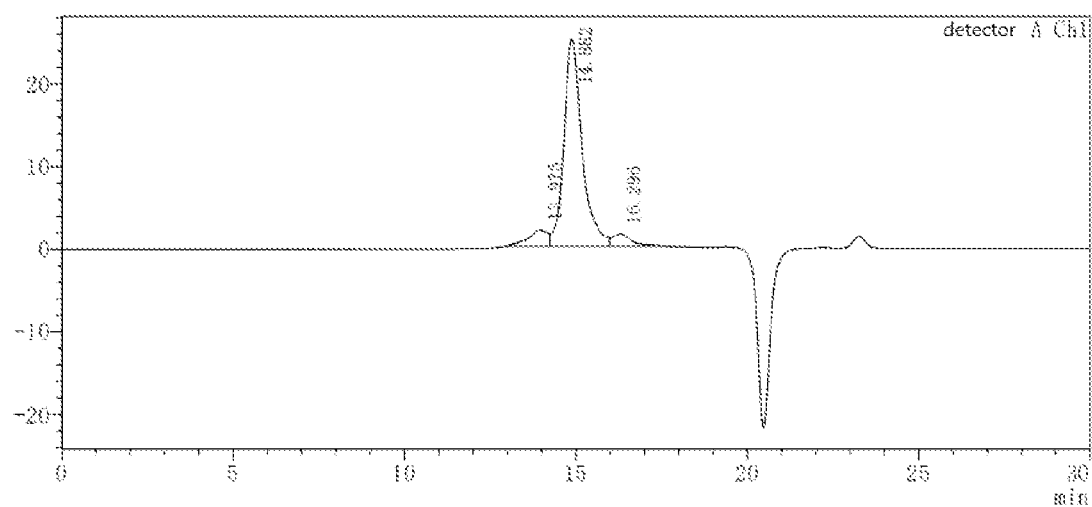

1 g of 8ARM(TP)-MAL-40K and 10 mg of hydroquinone were weighed and put into 50 ml single mouth round-bottomed flask and dissolved by 10 ml of dichloromethane. In addition, 1 g of 8ARM(TP)-MAL-40K were weighed and put into a 50 ml single mouth round-bottomed flask and dissolved by 10 ml dichloromethane. After the two systems were placed under an incandescent lamp for 48 hours, 40 mg thiosalicylic acid was added respectively. The reaction lasted for two hours. Samples were taken for GPC test, the GPC test spectrum is shown in FIGS. 5A-5B, and the corresponding spectrum data are shown in Table 2 and Table 3. The GPC test results in Table 4 show that the purity of pharmaceutical conjugate in the reaction system with hydroquinone is 89.8%, and that in the reaction system without hydroquinone is 87%, and the percentages of the high molecular weight impurity and the low molecular weight impurity are less than those in the system without hydroquinone.

TABLE 2

| Peak number | Retention time | Area | Height | Concentration |
|---|---|---|---|---|
| 1 | 13.986 | 40155 | 1083 | 5.789 |
| 2 | 14.877 | 622103 | 16701 | 89.819 |
| 3 | 16.281 | 30363 | 962 | 4.384 |
| Total | | 692621 | 18747 | |

TABLE 3

| Peak number | Retention time | Area | Height | Concentration |
|---|---|---|---|---|
| 1 | 13.975 | 77989 | 1972 | 7.306 |
| 2 | 14.882 | 928480 | 25133 | 86.981 |
| 3 | 16.296 | 60980 | 1535 | 5.713 |
| Total | | 1067449 | 28640 | |

TABLE 4

| GPC test | Main product (%) | High molecular weight impurity (%) | Low molecular weight impurity (%) |
|---|---|---|---|
| With Hydroquinone | 89.8 | 5.8 | 4.4 |
| without Hydroquinone | 87 | 7.3 | 5.7 |

The above results show that the addition of polymerization inhibitor (such as hydroquinone) in the reaction system can improve the purity of pharmaceutical conjugate products.

The above is only the preferred embodiment of the present invention, and is not intended to limit the present invention. Any modifications, equivalent substitutions, etc., which are within the spirit and principles of the present invention, should be included in the scope of the present invention.

The invention claimed is:

1. A pharmaceutical conjugate, comprising a composition of a polyethylene glycol maleimide derivative and a polymerization inhibitor and a drug, wherein the mass ratio of the polymerization inhibitor to the polyethylene glycol maleimide derivative is ≥0.1 μg:1 g, the polyethylene glycol maleimide derivative contains at least one terminal maleimide group.

2. The pharmaceutical conjugate according to claim 1, wherein said polymerization inhibitor is selected from one or a combination of two or more of a radical polymerization inhibitor, a phenolic polymerization inhibitor, an inorganic compound polymerization inhibitor, and an organometallic compound polymerization inhibitor.

3. The pharmaceutical conjugate according to claim 1, wherein the mass ratio of the polymerization inhibitor to the polyethylene glycol maleimide derivative is from 0.1 μg to 10 mg:1 g.

4. The pharmaceutical conjugate according to claim 1, wherein the polyethylene glycol maleimide derivative has the following structure: PEG-X-MAL (I), wherein PEG is polyethylene glycol residue, X is a linking group of PEG and MAL, and is selected from: one or a combination of two or more of —(CH$_2$)$_r$—,

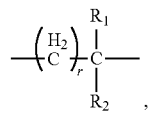

—(CH$_2$)$_r$O—, —(CH$_2$)$_r$CO—, —(CH$_2$)$_r$NH—, —(CH$_2$)$_r$CONH—, —(CH$_2$)$_r$NHCO—, —(CH$_2$)$_r$S—, —(CH$_2$)$_r$COO— and —(CH$_2$)$_r$OCO—, r is an integer from 0 to 10, MAL is a maleimide group

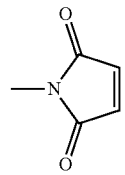

$R_1$ and $R_2$ are independently selected from: —H, a C1-6 alkyl group, a C1-6 alkoxy group, a C3-6 cycloalkyl group, and a C4-10 alkylene cycloalkyl group.

5. The pharmaceutical conjugate according to claim 4, wherein said X is selected from the group consisting of: a single bond, —CH$_2$—, —CH$_2$CH$_2$—, —CH$_2$CH$_2$CH$_2$—, —CH(CH$_3$)—, —CH$_2$CH(CH$_3$)—, —CH$_2$CH$_2$CH(CH$_3$)—, —(CH$_2$)$_r$O—, —(CH$_2$)$_r$CO—, —(CH$_2$)$_r$NH—, —(CH$_2$)$_r$CONH— and —(CH$_2$)$_r$NHCO—; and/or, the r is an integer from 0 to 5.

6. The pharmaceutical conjugate according to claim 4, wherein said PEG is a linear polyethylene glycol residue having a structure shown in formula II or III:

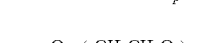

wherein p and q are independently selected from the group consisting of an integer of 1-2400; or, the PEG is a Y-shape or U-shape polyethylene glycol residue having a structure of formula IV or V:

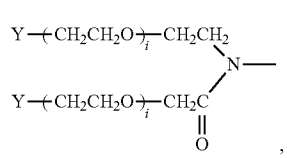

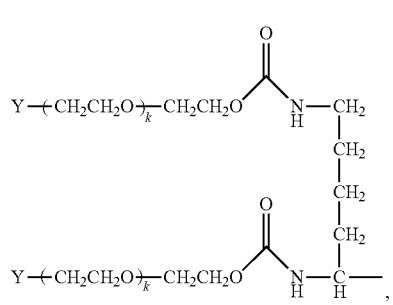

wherein i and k are independently selected from an integer of 1-1200;

or PEG is a multi-branched polyethylene glycol residue having the structure shown in formula VI:

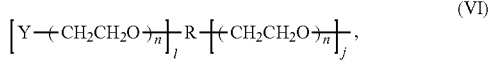  (VI)

wherein n is an integer from 1 to 800, 1 is an integer from 0 to 7, and j is an integer from 1 to 8, R is a core molecule of a multi-branched polyethylene glycol, and R is selected from the group consisting of: pentaerythritol, oligo-pentaerythritol, methyl glucoside, sucrose, diethylene glycol, propylene glycol, glycerol, and polyglycerol residues;

wherein Y is a terminal group selected from the group consisting of: C1-C6 alkoxy group, hydroxyl, carboxyl group, succinimide carbonate group, succinimide acetate group, succinimide propionate group, and succinimide succinate group, succinimide group, dithiopyridyl group, propionic acid group, aldehyde group, thiol ester group, acryloxy group, acrylic acid group, azido group, glutaric acid group, alkynyl, 4-nitrophenyl carbonate, silane, and carboxymethyl.

7. The pharmaceutical conjugate according to claim 6, wherein said polyethylene glycol maleimide derivative has the following structure:

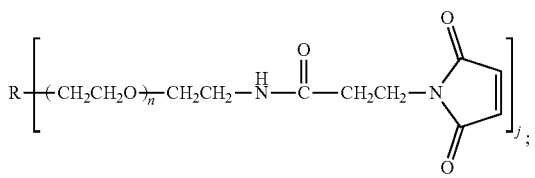  (VIII)

and, j=8, PEG is an eight-arm polyethylene glycol residue.

8. The pharmaceutical conjugate of claim 7 wherein R has the structure of formula IX or X:

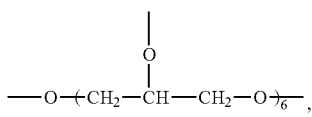  (IX)

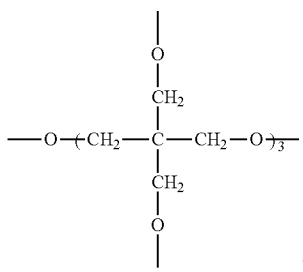  (X)

9. The pharmaceutical conjugate according to claim 6, wherein PEG has a molecular weight of from 1 to 80 kDa.

10. The pharmaceutical conjugate according to claim 2, wherein the radical polymerization inhibitor is selected from one or more of 1,1-diphenyl-2-trinitrophenylhydrazine, 4,4'-dimethoxydiphenyl oxynitride, 4,4'-dinitrodiphenyl oxynitride, di-tert-butyl oxynitride, 2,2,6,6-tetramethyl-4-hydroxyl piperidine oxynitride and benzoyl peroxide;

and/or said phenolic polymerization inhibitor is selected from one or more of: hydroquinone, methyl hydroquinone, p-tert-butylcatechol, 2-tert-butyl hydroquinone, 4-methoxyphenol, 2,5-di-tert-butyl hydroquinone, 2,6-di-tert-butyl-4-methylphenol, 4,4'-dihydroxybiphenyl, pyrogallol and bisphenol A;

and/or said inorganic compound polymerization inhibitor is selected from one or more of: ferric chloride, cuprous chloride, copper chloride, copper sulfate, titanium trichloride, titanium chloride, sodium sulfate, sodium sulfide and ammonium thiocyanate;

and/or said organometallic compound polymerization inhibitor is selected from one or more of: naphthenic acid copper, chromium acetate, nickel acetate, copper dimethyldithioformate, and copper dit-butyldithiocarbamate.

11. The pharmaceutical conjugate according to claim 1, wherein the radical polymerization inhibitor is 1,1-diphenyl-2-trinitrophenylhydrazine; and/or, the phenolic polymerization inhibitor is hydroquinone or p-tert-butyl phenol; and/or the inorganic compound polymerization inhibitor is copper chloride; and/or the organometallic compound polymerization inhibitor is nickel acetate.

12. The pharmaceutical conjugate according to claim 1, wherein the polymerization inhibitor is a phenolic polymerization inhibitor.

13. The pharmaceutical conjugate according to claim 1, wherein the polymerization inhibitor is selected from one or more of: hydroquinone, methyl hydroquinone, p-tert-butylcatechol, 2-tert-butyl hydroquinone, 4-methoxyphenol, 2,5-di-tert-butyl hydroquinone, 2,6-di-tert-butyl-4-methylphenol, 4,4'-dihydroxybiphenyl, pyrogallol and bisphenol A.

14. The pharmaceutical conjugate according to claim 1, wherein the polymerization inhibitor is hydroquinone or p-tert-butyl-phenol.

15. The pharmaceutical conjugate according to claim 1, wherein the drug is selected from the group consisting of amino acids, polypeptides, proteins, sugars, organic acids, alkaloids, flavonoids, terpenoids, terpenoids, phenylpropanoid phenols, steroids and steroids.

16. The pharmaceutical conjugate according to claim 15, wherein the drug is a polypeptide or protein drug.

17. The pharmaceutical conjugate according to claim 16, wherein the polypeptide or protein drug contains free sulfhydryl groups; and/or, a sulfhydryl group is introduced at a specific site in the polypeptide or protein drug.

* * * * *